US012599409B2

(12) United States Patent
Ziran et al.

(10) Patent No.: US 12,599,409 B2
(45) Date of Patent: Apr. 14, 2026

(54) HINGE APPARATUS FOR EXTERNAL BONE FIXATOR

(71) Applicant: ADVANCED TRAUMA SOLUTIONS, LLC, Decatur, GA (US)

(72) Inventors: Bruce H. Ziran, Decatur, GA (US); Patrick Kelly Capeheart, Dahlonega, GA (US)

(73) Assignee: ADVANCED TRAUMA SOLUTIONS, LLC, Decatur, GA (US)

( * ) Notice: Subject to any disclaimer, the term of this patent is extended or adjusted under 35 U.S.C. 154(b) by 0 days.

(21) Appl. No.: 18/943,039

(22) Filed: Nov. 11, 2024

(65) Prior Publication Data

US 2025/0064482 A1 Feb. 27, 2025

Related U.S. Application Data

(60) Continuation-in-part of application No. 18/120,042, filed on Mar. 10, 2023, which is a division of application No. 17/524,285, filed on Nov. 11, 2021, now Pat. No. 11,660,122.

(60) Provisional application No. 63/163,146, filed on Mar. 19, 2021.

(51) Int. Cl.
*A61B 17/64* (2006.01)

(52) U.S. Cl.
CPC ........ *A61B 17/6458* (2013.01); *A61B 17/645* (2013.01)

(58) Field of Classification Search
CPC ....... A61B 17/60; A61B 17/64; A61B 17/606; A61B 17/6458
See application file for complete search history.

(56) References Cited

U.S. PATENT DOCUMENTS

| | | | | |
|---|---|---|---|---|
| 5,947,671 A * | 9/1999 | Kanaan | ..................... | G05G 1/10 |
| | | | | 74/555 |
| 10,136,919 B2 * | 11/2018 | Muniz | .................. | A61B 17/645 |
| 10,568,662 B2 * | 2/2020 | Nemovicher | ...... | A61B 17/6466 |
| 11,627,991 B2 * | 4/2023 | Kent | .................. | A61B 17/6416 |
| | | | | 606/54 |
| 2019/0110814 A1 * | 4/2019 | Nemovicher | .......... | A61B 90/57 |
| 2022/0133356 A1 * | 5/2022 | Sanders | ............ | A61B 17/6458 |
| | | | | 606/54 |

* cited by examiner

*Primary Examiner* — Ellen C Hammond
(74) *Attorney, Agent, or Firm* — Thomas I Horstemeyer, LLP

(57) ABSTRACT

A hinge apparatus has a pair of outrigger bars that attach to and extend outwardly from respective joint bodies. The outrigger bars can be adjusted at various angles relative to each other. The joint bodies have respective surfaces that face and engage each other. A joint screw connects the joint bodies. A torque amplifying knob with collapsable turn levers rotates a central screw turn actuator. The actuator is engaged with the screw so that movement of the actuator is caused in opposite first and second linear directions along the threaded body when rotational force is applied in opposite first and second rotational directions, respectively, to the torque amplifying knob. The turn levers of each knob can be collapsed in a side-by-side arrangement. The turn levers of the knobs are ergonomically designed so that the knobs can be hand operated, without tools, in the collapsed and uncollapsed configurations.

14 Claims, 10 Drawing Sheets

10

10

HINGE APPARATUS FOR EXTERNAL BONE FIXATOR

CLAIM OF PRIORITY

This application is a continuation-in-part (CIP) of application Ser. No. 18/120,042, filed Mar. 10, 2023, which is a division of Ser. No. 17/524,285, filed Nov. 11, 2021, now U.S. Pat. No. 11,660,122, which claims the benefit of provisional application No. 63/163,146, filed Mar. 19, 2021, all of the foregoing of which are incorporated herein by reference in their entireties.

RELATED APPLICATIONS

This application is related to copending application "Multi-Clamp Apparatus For External Bone Fixator, application no. TBA, filed on even date herewith, which is incorporated herein by reference in its entirety.

FIELD OF THE INVENTION

The embodiments of the present disclosure generally relate to the medical field of bone fractures and deformity, and more particularly, to multi-purpose external fixators that are used for stabilizing fractures in patients.

BACKGROUND OF THE INVENTION

In the medical field of orthopedics, for several years a technique has been known for stabilizing fractures by using external fixators instead of conventional plaster casts. External fixators usually comprise a plurality of threaded bone pins, or screws, normally in pairs, which are implanted in the bone fragments of the fracture in such a way that the head ends of the bone pins project from the skin of the patient. The ends are anchored to a rigid external frame which is equipped with clamps and outrigger bars, which can be orientated in such a way as to allow them to be adjusted to the position of the bone pins.

The bone pins usually have a cylindrical body, delimited on one side by a threaded end designed to be screwed into the bone fragment, and on the other side by the above-mentioned head end, which is shaped in such a way that it can be connected to a temporary grip that allows the pin to be screwed into the bone fragment. The connection between the pin and the grip is normally of the male-female type with quick coupling and release or another conventional mechanical interface.

During its application the pins are placed on opposite sides of the fracture span and connect to a clamp that allows connectivity between pins. Then the surgeon connects the pins, clamps, and a series of bars together. If necessary, the surgeon then aligns the limb for either temporary or permanent positioning. In most cases, the alignment is also to stabilize the body part to prevent further damage, and allow transport to a different level of care, or to allow the injury to evolve and ultimately allow a safer invasive procedure (damage control, often called "reduction").

Once the fracture has been reduced, the surgeon locks the joints and clamps to hold the bone fragments in the predetermined position, thus allowing the correct alignment between the bone fragments, which through the formation of "bone callus", gradually restores the lamellar bone tissue with which the bone recovers its original continuity and functionality.

The use of external fixators was extended to a vast range of orthopedic operations, such as limb lengthening, correction of bone axis rotary and angular deformities, pseudarthrosis, etc. In other words, external fixators are today used as multi-purpose orthopedic devices, both to correct deformations caused by trauma and to correct pathological deformations.

U.S. Pat. No. 9,155,560, which is incorporated herein by reference, discloses an example, among others, of a multi-purpose external fixator that has a universal clamp apparatus. The universal clamp apparatus has parallel first and second clamps, each having a pair of channels, one that is sized to receive and attach to a outrigger bar associated with a frame of the fixator and another that is sized to receive and attach to a bone pin. A collapsible handle with cam mechanism is employed to selectively either secure or unsecure the frame outrigger bar and/or bone pin in the first and second clamps. When the handle is closed, the frame outrigger bar and/or bone pin are squeezed and secured in the respective channels. A primary disadvantage of this universal clamp apparatus is that when the handle is closed, the first and second clamps have an imprecise fixed degree of tightness with respect to the outrigger bar and/or bone pin. This results in an inability to properly secure the frame outrigger bar and/or bone pin as well as readjust the squeezing tightness, when necessary. Furthermore, there is a risk that the collapsible handle could catch an object and get loosened, thereby causing the clamp to lose stability.

Other fixators have utilized a progressive tightening, usually through the use of a compressive screw design. These fixators typically require the use of a tool, such as a wrench, to tighten and loosen the clamp. In the surgical arena, the tool is often part of a "set" of instruments that requires sterilization. Without the tool, the clamp tightening can be compromised, even when provisional texturing of the clamp allows some "hand tightening". When these fixators are used in austere environments (i.e. warfare, rural and underserved areas), the tool may be lost and the utility of the fixator is compromised.

Commonly assigned U.S. Pat. No. 11,660,122, which is incorporated herein by reference, discloses a universal clamp apparatus for a bone fixation device that uses progressive tightening and that can be operated without the need for any tools. The universal clamp apparatus has at least one pin/outrigger bar clamp, but preferably two pin/outrigger bar clamps. Each clamp has seating grooves for snapping in and attaching to at least one of the following: a frame outrigger bar associated with a frame of the fixator and/or a bone pin for implantation in a bone fragment. A screw mechanism, such as a clamp screw, extends through and connects the first and second pin/outrigger bar clamps. An ergonomically designed knob having at least one collapsible or non-collapsible turn lever acts as a torque amplifier when rotated to tighten and untighten the pin/outrigger bar clamps to the frame outrigger bar and/or bone pin by movement along the clamp screw. A planar side of the pin/outrigger bar clamps that are contiguous each have radial ratchet grooves that are in mating engagement and that implement a ratcheting and securing mechanism so that the rotation of the pin/outrigger bar clamps relative to each other occurs in discrete incremental rotational steps.

SUMMARY OF THE INVENTION

Various embodiments of a hinge apparatus for an orthopedic exterior fixator are disclosed.

In one embodiment, among others, the hinge apparatus has first and second outrigger bars that attach to and extend outwardly from first and second joint bodies. The outrigger bars can be adjusted at various angles relative to each other. The first and second joint bodies have respective first and second surfaces that face and engage each other. A joint screw connects the first and second joint bodies. A torque amplifying knob with collapsible turn levers rotates a central screw turn actuator. The central screw turn actuator is engaged with the joint screw so that movement of the actuator is caused in opposite first and second linear directions along the cylindrical threaded body when rotational force is applied in opposite first and second rotational directions, respectively, to the torque amplifying knob. The turn levers of each knob can be collapsed in a generally mating, side-by-side arrangement. The turn levers of the knobs are ergonomically designed so that the knobs can be hand operated, without tools, in the collapsed and un-collapsed configurations.

Other embodiments, apparatus, methods, features, and advantages of the present invention will be apparent to one with skill in the art upon examination of the following drawings and detailed description. It is intended that all such additional embodiments, apparatus, methods, features, and advantages be included within this disclosure, be within the scope of the present invention, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE PREFERRED EMBODIMENT(S)

Figure 1:
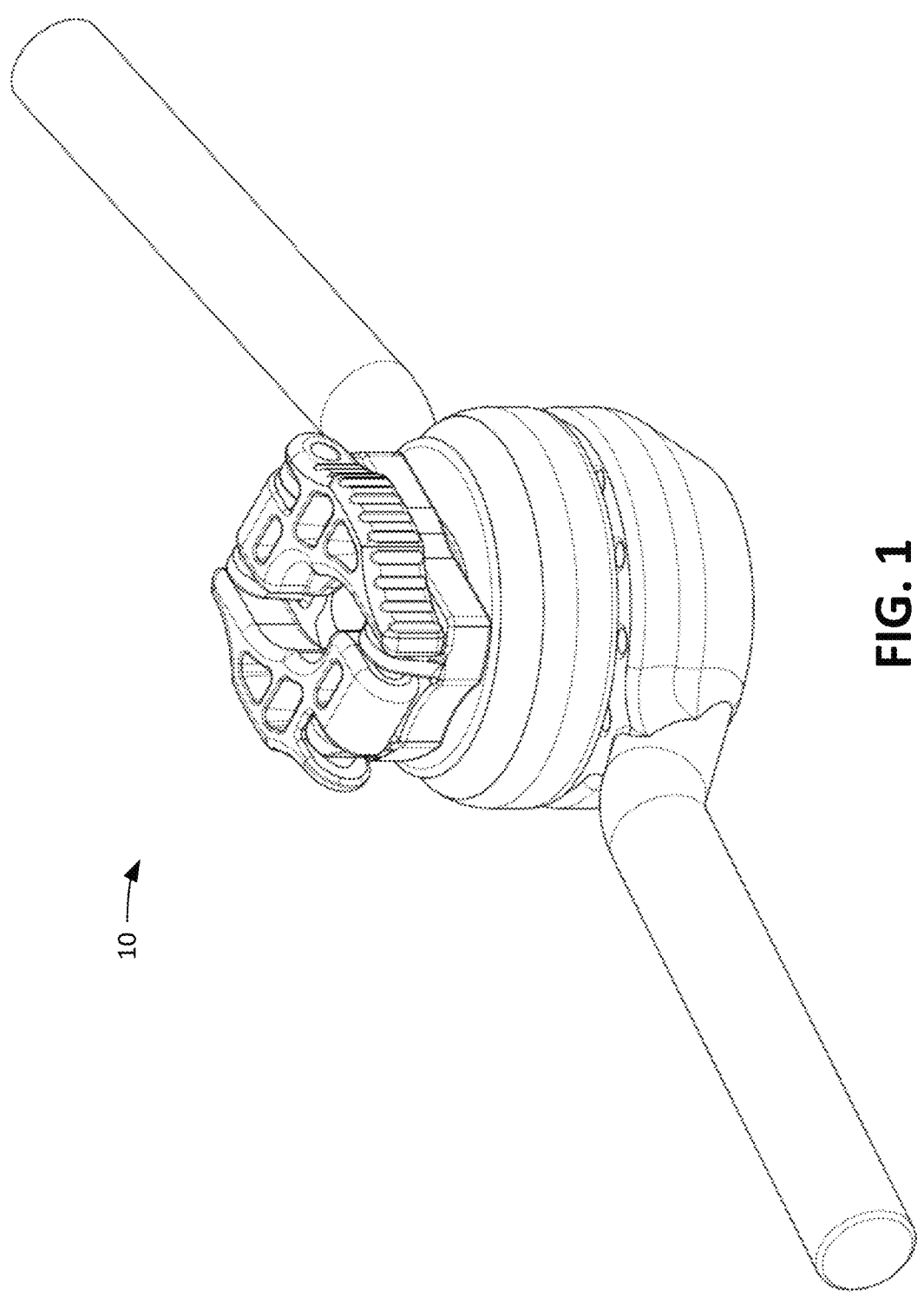
FIG. 1 is a perspective view of a hinge apparatus for an orthopedic external bone fixator with turn levers of a torque amplifying knob in a collapsed configuration, in accordance with an embodiment, among others, of the present invention.
Figure 2:
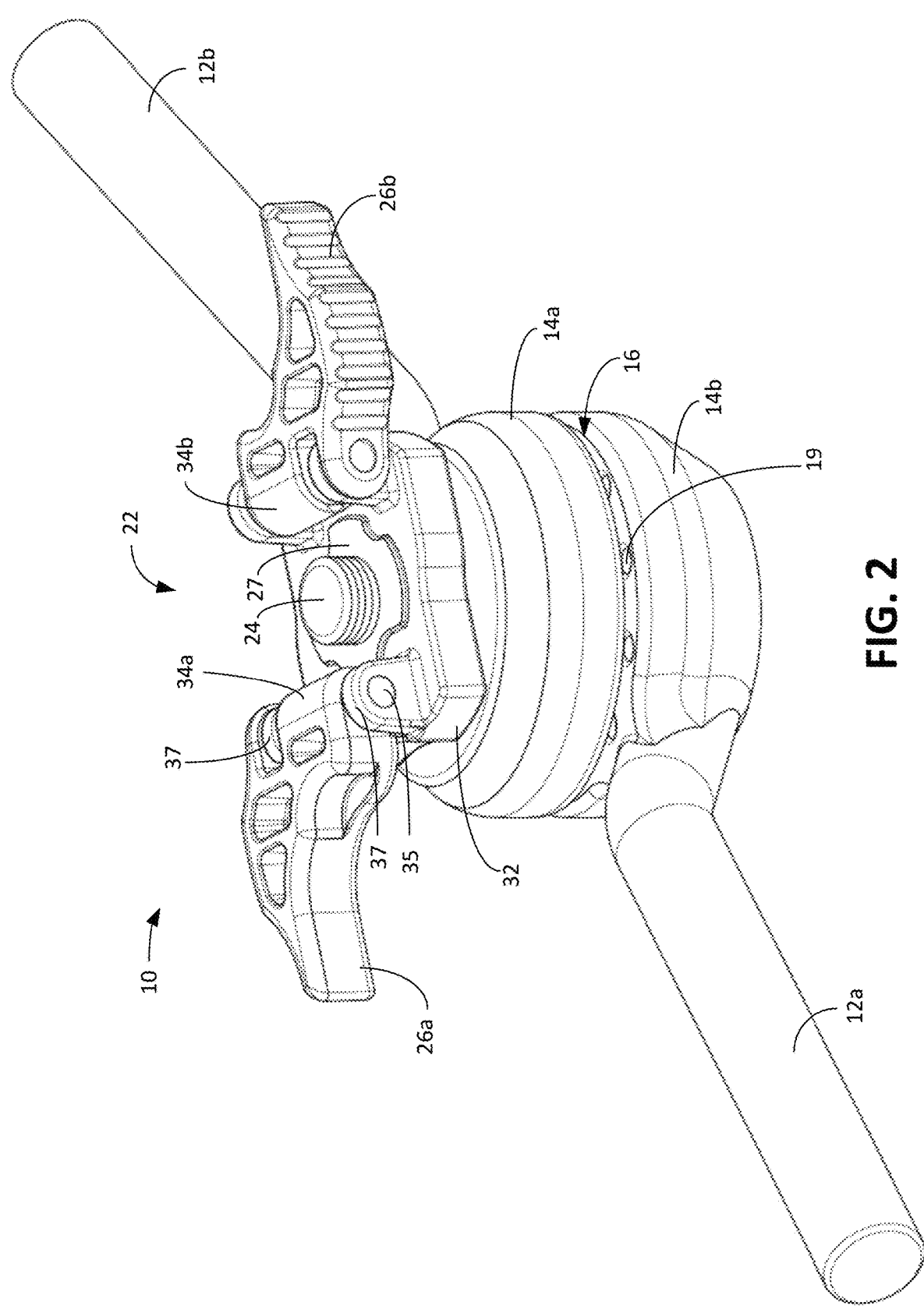
FIG. 2 is a perspective view of the hinge apparatus of FIG. 1 with turn levers in a un-collapsed configuration.
Figure 3:
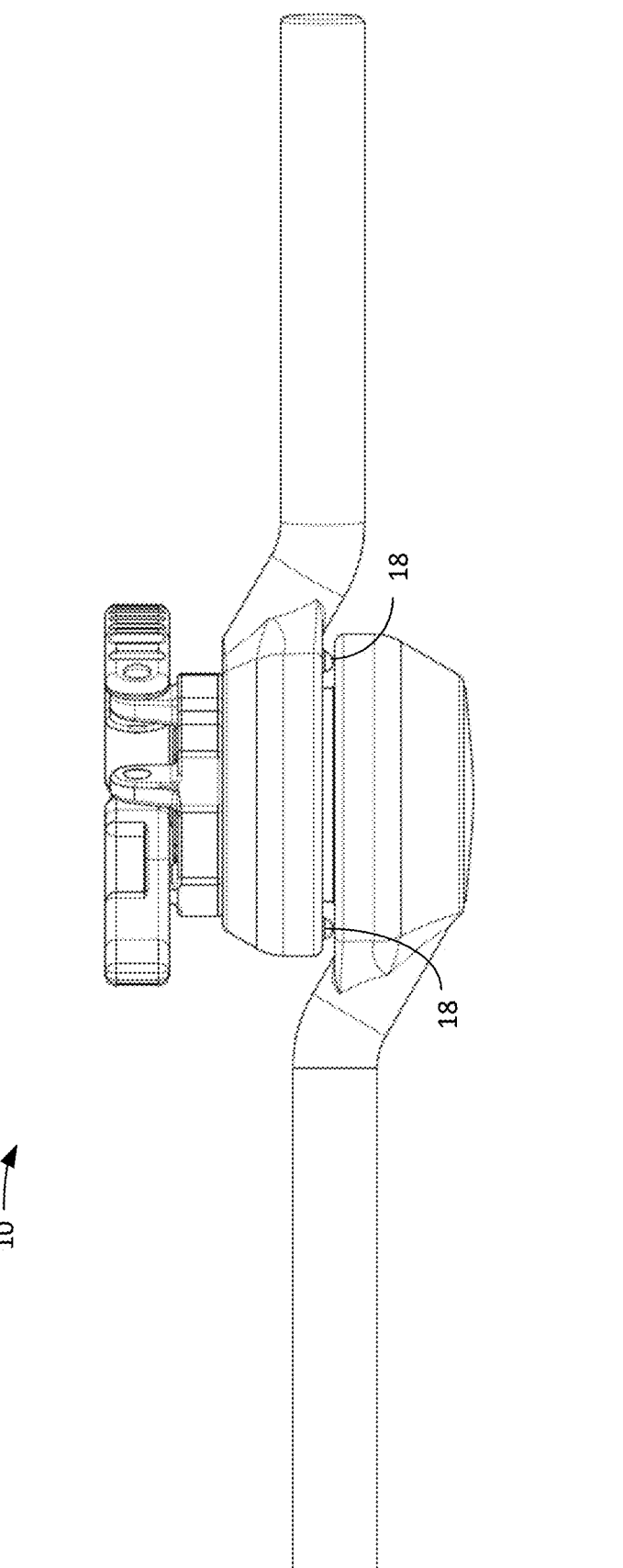
FIG. 3 is a front side view of the hinge apparatus of FIG. 1.
Figure 4:
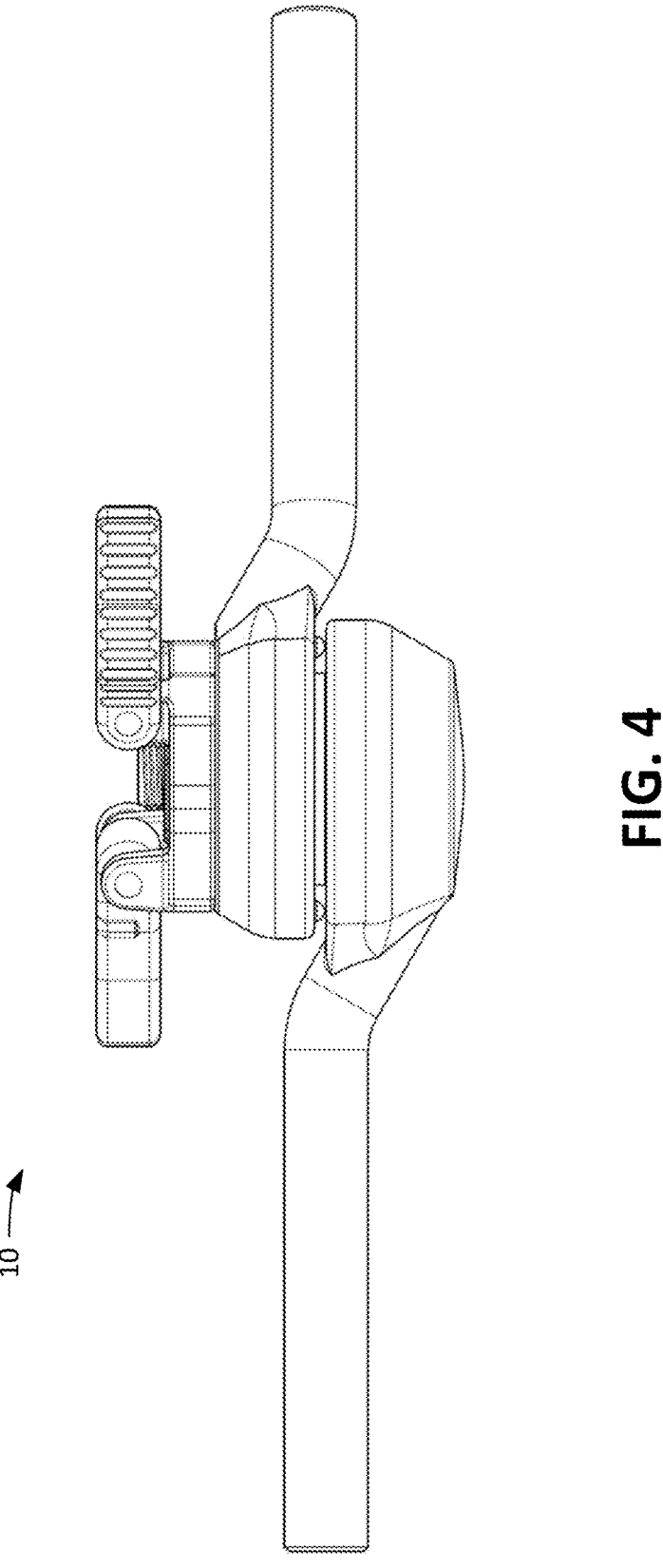
FIG. 4 is a front side view of the hinge apparatus of FIG. 2.
Figure 5:
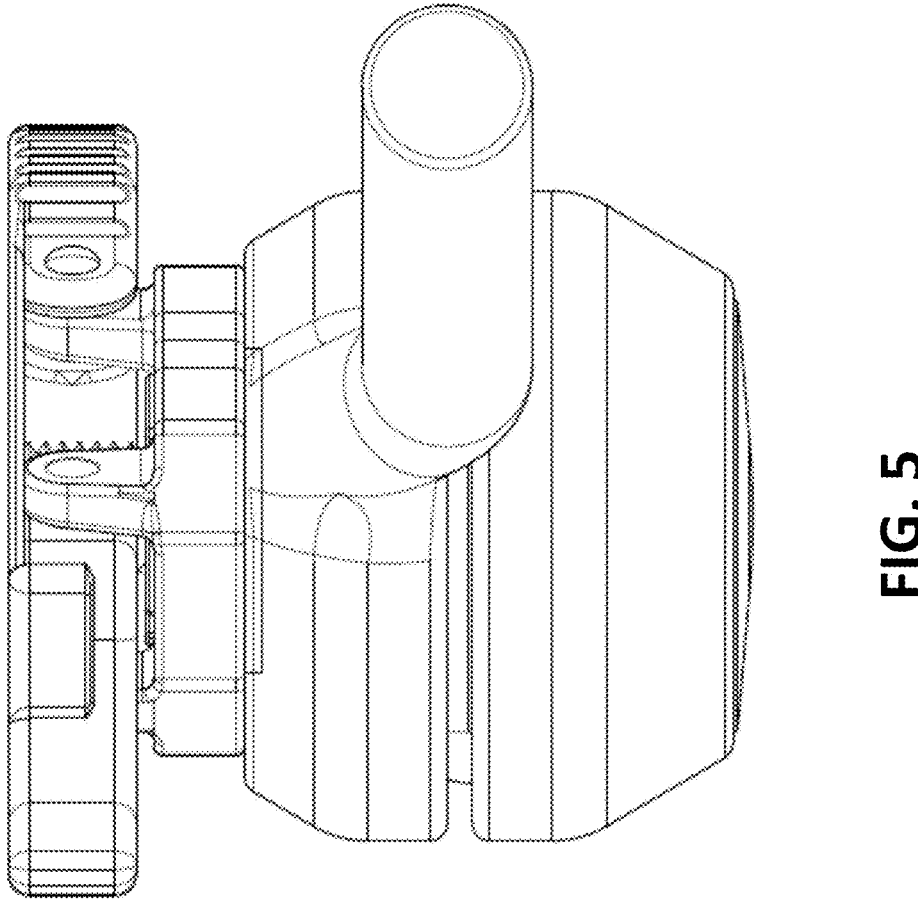
FIG. 5 is a side view of the hinge apparatus of FIG. 1.
Figure 5:
Figure 6:
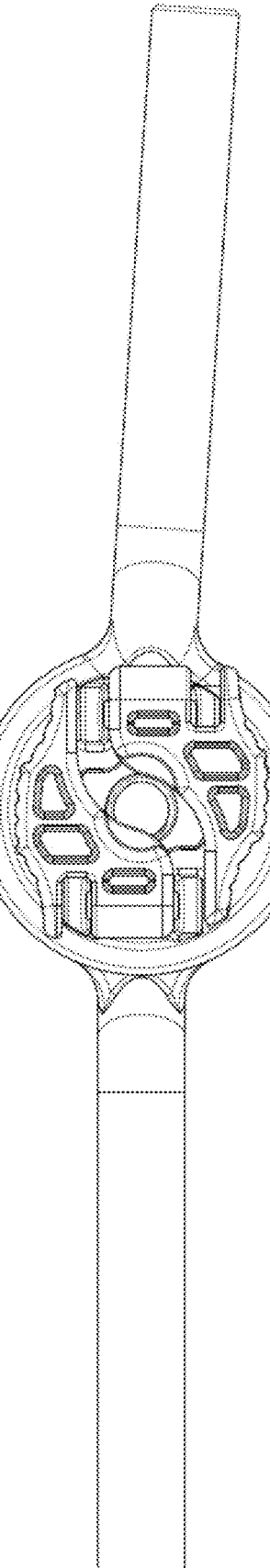
FIG. 6 is a top view of the hinge apparatus of FIG. 1.
Figure 7:
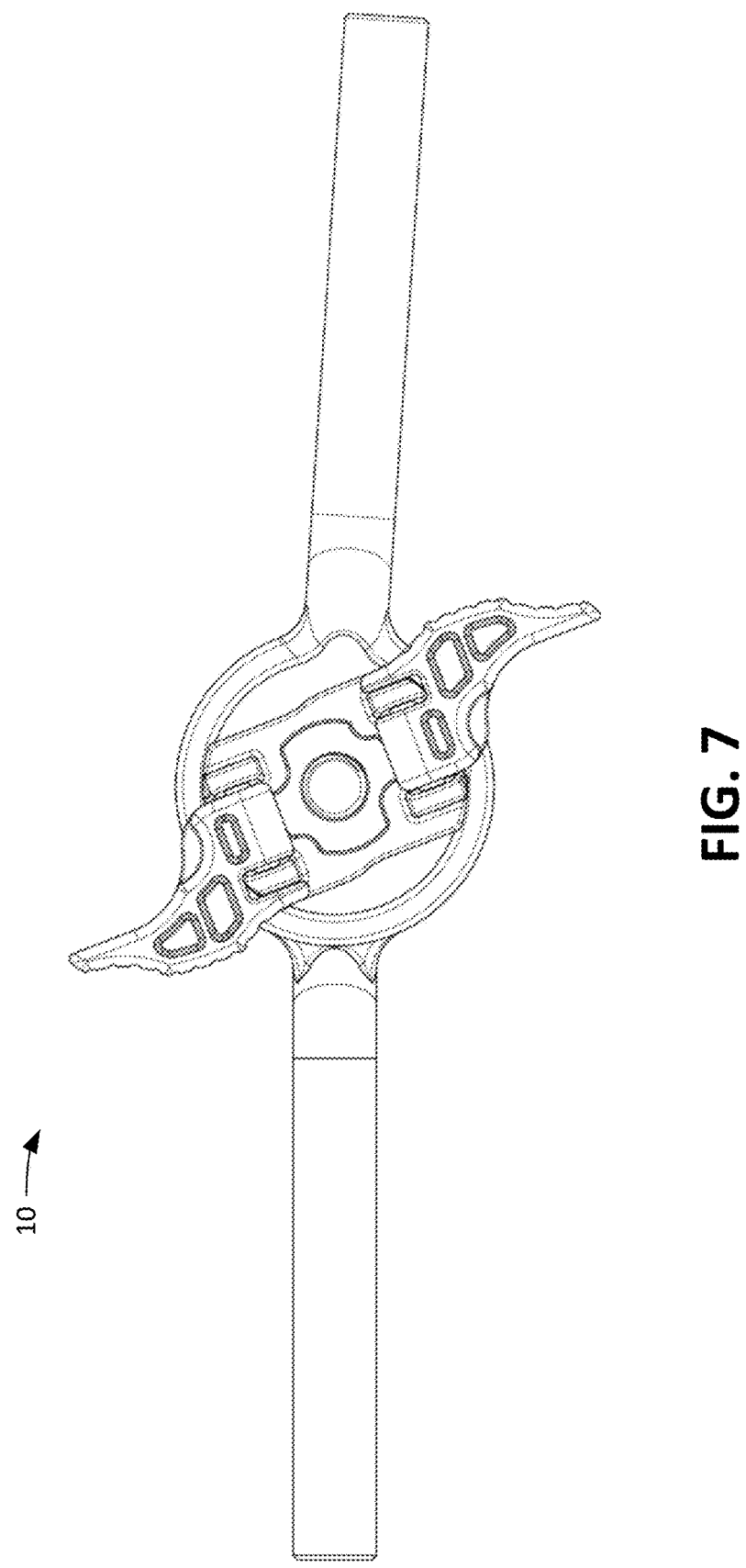
FIG. 7 is a top view of the hinge apparatus of FIG. 2.
Figure 8:
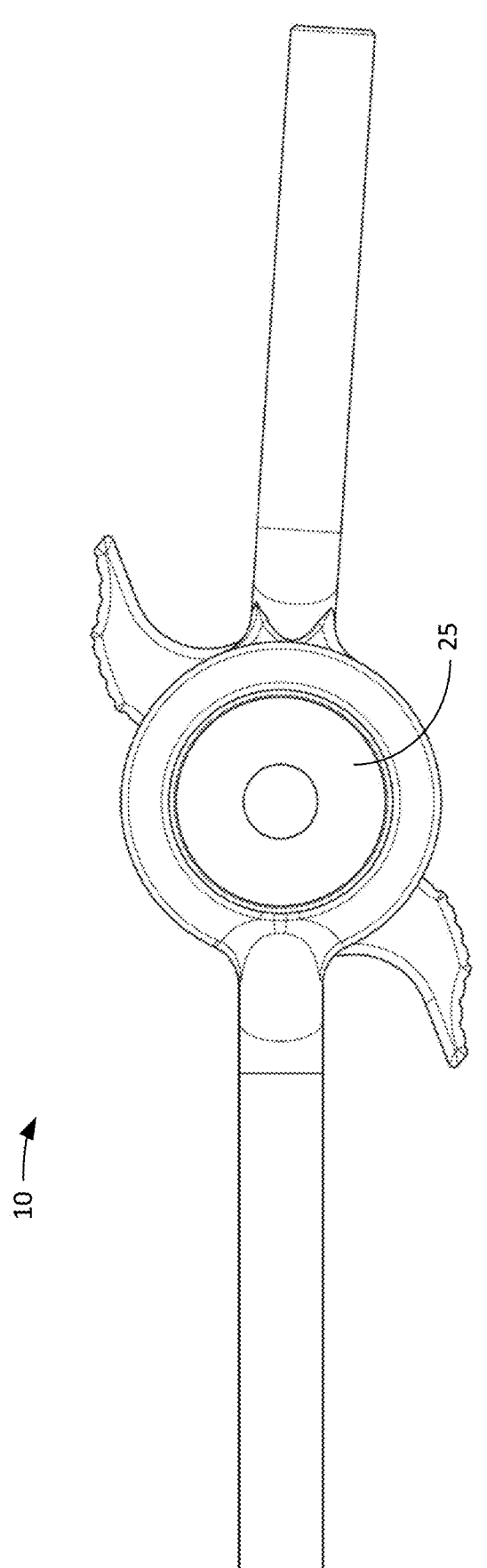
FIG. 8 is a bottom view of the hinge apparatus of FIG. 2.
Figure 9:
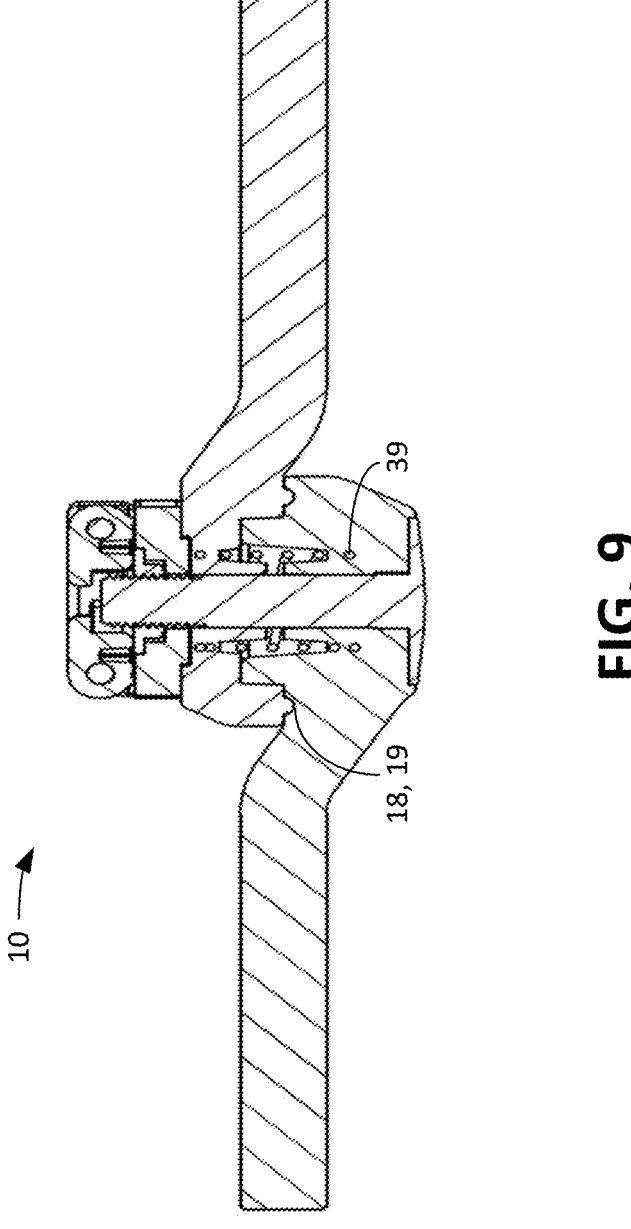
FIG. 9 is a cross-sectional view of the hinge apparatus of FIG. 1.
Figure 10:
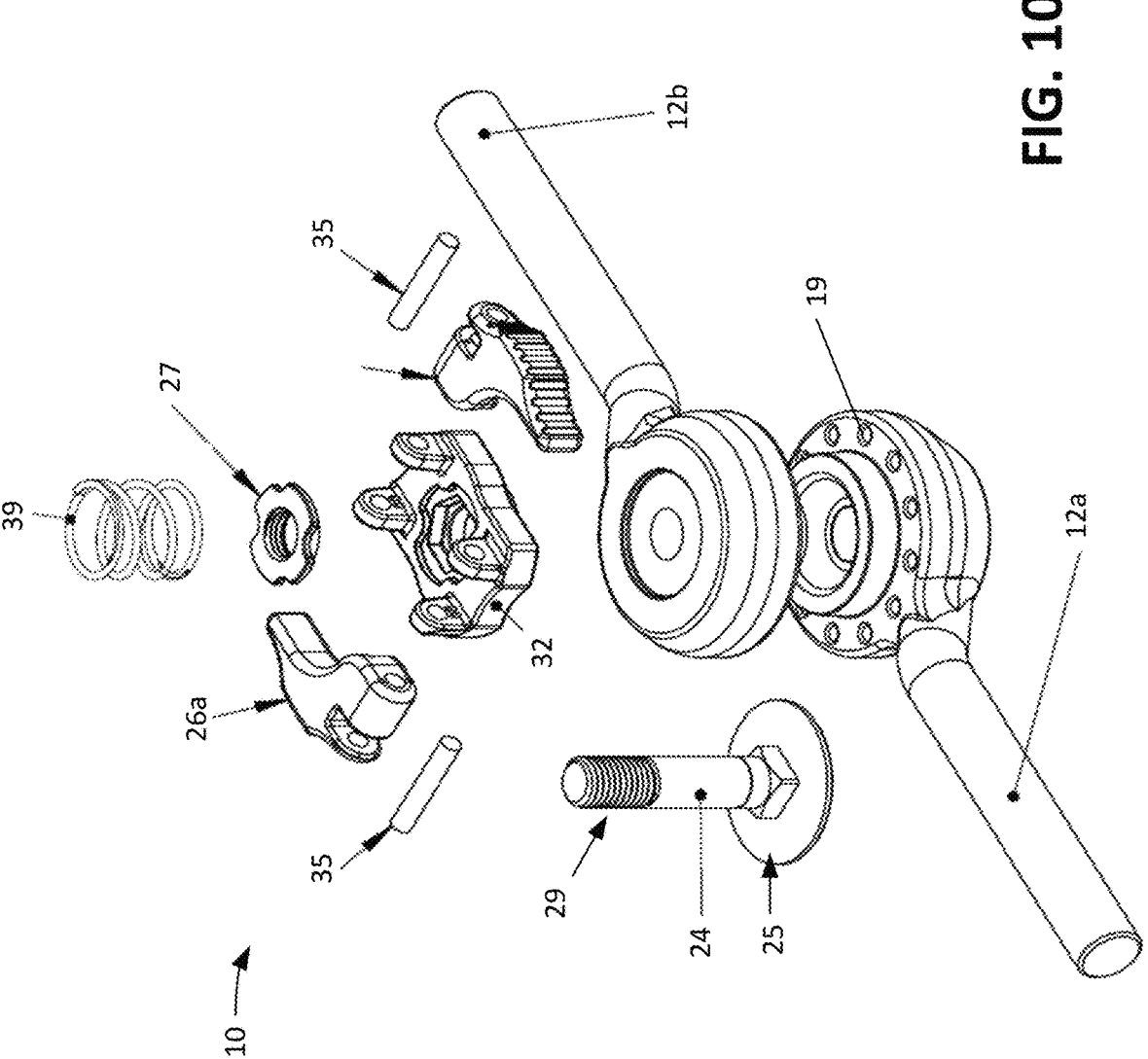
FIG. 10 is an exploded view of the hinge apparatus of FIG. 1.

A preferred embodiment, among other possible embodiments, of a hinge apparatus 10 for an orthopedic exterior fixator is shown in FIGS. 1-10.

The hinge apparatus 10 has first and second outrigger bars 12a, 12b, each outrigger bar 12a, 12b having an elongated longitudinal body extending between a connected end and a distal end. The outrigger bars 12a. 12b can be adjusted at various angles relative to each other and securely fixed at such angles. The outrigger bars 12a. 12b can be used for attachment of other fixator components. As examples, one or both of the outrigger bars 12a, 12b can be attached to a bone pin or another bar using a clamp, such as the universal clamp described and shown in U.S. Pat. No. 11,660,122. Also, preferably, each outrigger bar 12a, 12b has an internal reinforcement with a metallic core to enhance strength and are made from a material that is not subject to an induced current in a magnetic field.

The connected ends of the first and second outrigger bars 12a, 12b comprise respective first and second joint bodies 14a, 14b with respective first and second surfaces that face and engage with each other.

A hinge lock 16 is provided that has a plurality of outwardly extending, hemispherical, convex nubs 18 in the first joint body 14a that (1) are extendable into a plurality of inwardly extending, hemispherical, concave recesses 19 when a torque amplifying knob 22 is rotated in a first direction in order to lock the joint bodies 14a, 14b together and (2) are retractable from the plurality of concave recesses 19 when the torque amplifying knob 22 is rotated in the second direction in order to unlock the joint bodies 14a, 14b and permit relative rotation of the joint bodies 14a, 14b. In the preferred embodiment, the nubs 18 and recesses 19 are spaced apart in a circular manner every thirty degrees. The spacing enables the outrigger bars 12a, 12b to be moved and fixed relative to each other in thirty degree increments.

The hinge apparatus 10 further includes a joint screw 24 having an elongated cylindrical body extending along a screw axis. The joint screw 24 extends through and connects the joint bodies 14a, 14b, which are connected to the connected ends of the first and second outrigger bars 12a, 12b. The joint screw 24 has a screw head 25 and a a male threaded body 29. A female threaded base nut 27 is provided of a shape and size to move along the threaded body 29.

The torque amplifying knob 22 has at least one, but preferably a plurality, of collapsible turn levers 26a, 26b. Each turn lever 26a, 26b has a longitudinal body extending between a movable end and a hinged end.

The turn levers 26a, 26b are collapsed in a side-by-side arrangement. Each of the longitudinal bodies of the turn levers 26a, 26b have inner and outer edges. The inner edges are closer to the screw axis than the outer edges. The inner edges have respective contours that mate in complimentary manner when the turn levers 26a, 26b are collapsed in the side-by-side arrangement. The longitudinal bodies have sufficient size to cover a substantial part of the outer side of the central screw turn actuator 32 when the turn levers 26a, 26b are collapsed.

An important feature of the hinge apparatus 10 is that the knob 22 and turn levers 26a, 26b are designed ergonomically so that the knob 22 can be easily hand operated when the levers 26a, 26b are in the collapsed or un-collapsed configurations.

It should be noted that any of the torque amplifying knobs described and/or illustrated in commonly assigned U.S. Pat. No. 11,660,122, can be implemented on the hinge apparatus 10.

A central screw turn actuator 32 has an outer side and an inner side. The hinged end of each turn lever being connected via a hinge 34a, 34b to the outer side of the central screw turn actuator 32. Each hinge 34a, 34b has a pin 35 extending from a corresponding lever and passes through a pair of knuckles 37. The movable end of each turn lever 26a, 26b is movable between a collapsed position where each lever 34a, 34b is situated over the outer side of the central screw turn actuator 32 and an un-collapsed position where the movable end is situated outwardly from the outer side of the central screw turn actuator 32. The central screw turn actuator 32 is engaged with the joint screw 24 via nut 27 so that movement of the actuator 32 is caused in opposite first and second linear directions along the cylindrical threaded body when rotational force is applied in opposite first and second rotational directions, respectively, to the torque amplifying knob 22.

The hinge apparatus 10 can be viewed as having a size changeable knobs 22. The knob 22 is designed to change between a first size and a second size. The first size has at least a part that extends a greater distance in a direction outwardly from the threaded body of the screw 24 as compared to the second size so that a greater rotational torque can be applied relative to the screw 24 in connection with the first size as compared to the second size.

In the preferred embodiment, the base nut 27 is noncircular around its periphery in that the nut 27 has four equally spaced, outwardly, radially extending nubs that enable the actuator 32, which have corresponding apertures to match the nut periphery, to impose rotational force on the base nut 27. The central screw turn actuator 32 is designed to rotate the 27 so that the actuator 27 is moved along the screw 24.

In other alternative embodiments, the screw turn actuators 32 can be designed, without the base nut 27, to rotate a head associated with the screw that is threaded into a nut or other structure in or associated with the opposing joint body 14*b*. In yet other alternative embodiment, the screw turn actuator 32 can be designed with a female threaded part, without the respective base nut 27 to rotate along the male threaded screw 24.

Each hinge 34*a*, 34*b* pivots about a hinge longitudinal body. The hinge longitudinal bodies are parallel to one another and extend perpendicular to the screw 24. The screw axis is generally centered between the hinge longitudinal bodies.

In the preferred embodiment of the hinge apparatus 10, the hinge apparatus 10 includes at least one spring 39, such as a compression spring, that applies constant separation force to separate the joint bodies 14*a*, 14*b*. The screw 24 passes through the spring 39. In essence, the spring 39 imposes a separation force between the first and second surfaces of the respective first and second joint bodies 14*a*, 14*b*. The compression spring 39 enables easier operation.

Finally, it should be emphasized that the above-described embodiments of the present invention, particularly, any "preferred" embodiments, are merely possible nonlimiting examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention.

At least the following is claimed:

1. A hinge apparatus for an orthopedic exterior fixator, the hinge apparatus comprising:

first and second outrigger bars, each of the first and second outrigger bars having an elongated longitudinal body extending between a connected end and a distal end;

first and second joint bodies, each of the first and second joint bodies being attached to a respective one of the connected ends, the first and second joint bodies having respective first and second surfaces that face and engage each other;

a joint screw having an elongated cylindrical threaded body extending along a screw axis, the joint screw extending through and connecting the first and second joint bodies;

a torque amplifying knob, the knob having a plurality of collapsible turn levers, each turn lever having a longitudinal body extending between a movable end and a hinged end; and a central screw turn actuator, the central screw turn actuator having an outer side and an inner side, the hinged end of each turn lever being connected via a hinge to the outer side of the central screw turn actuator, the movable end of each turn lever being movable between a collapsed position where each lever is situated over the outer side of the central screw turn actuator and an un-collapsed position where the movable end is situated outwardly from the outer side of the central screw turn actuator, the central screw turn actuator engaged with the joint screw so that movement of the actuator is caused in opposite first and second linear directions along the cylindrical threaded body when rotational force is applied in opposite first and second rotational directions, respectively, to the torque amplifying knob.

2. The apparatus of claim 1, further comprising a hinge lock having a plurality of convex nubs in the first joint body (a) that are extendable into a plurality of concave recesses when the torque amplifying knob is rotated in the first direction in order to lock the joint bodies together and (b) that are retractable from the plurality of concave recesses when the torque amplifying knob is rotated in the second direction in order to unlock the joint bodies and permit relative rotation of the joint bodies.

3. The apparatus of claim 1, wherein each hinge pivots about a hinge longitudinal body, the hinge longitudinal bodies being parallel to one another and extending perpendicular to the screw, the screw axis being generally centered between the hinge longitudinal bodies.

4. The apparatus of claim 1, wherein the turn levers are collapsed in a side-by-side arrangement.

5. The apparatus of claim 4, wherein each of the longitudinal bodies of the turn levers have inner and outer edges, the inner edges being closer to the screw axis than the outer edges, the inner edges having respective contours that mate in complimentary manner when the turn levers are collapsed in the side-by-side arrangement, the longitudinal bodies having sufficient size to cover a substantial part of the outer side of the central screw turn actuator when the turn levers are collapsed.

6. The apparatus of claim 1, wherein the joint screw further comprises a screw head and a threaded nut of a shape and size to move along the threaded body, and wherein the central screw turn actuator engages the screw, and an underside of the screw head is secured to the one of the first and second arms that is furthest away from the central screw turn actuator.

7. The apparatus of claim 1, further comprising a spring that imposes a separation force between first and second surfaces of the respective first and second joint bodies.

8. A hinge apparatus for an orthopedic exterior fixator, the hinge apparatus comprising:

first and second outrigger bars, each of the first and second outrigger bars having an elongated longitudinal body extending between a connected end and a distal end;

first and second joint bodies, each of the first and second joint bodies being attached to a respective one of the connected ends, the first and second joint bodies having respective first and second surfaces that face and engage each other;

a joint screw having an elongated cylindrical threaded body extending along a screw axis, the joint screw extending through and connecting first and second joint bodies;

a size changeable knob, the size changeable knob designed to change between a first size and a second size, the first size having at least a part that extends a greater distance in a direction outwardly from the threaded body of the joint screw as compared to the second size so that a greater rotational torque can be applied relative to the screw in connection with the first size as compared to the second size, the knob having a central screw turn actuator engaged with the joint screw so that movement of the actuator is caused in first and second linear directions along the cylindrical threaded body when rotational force is applied in first and second rotational directions, respectively, to the size changeable knob; and wherein the size changeable knob includes at least one collapsible turn lever, the turn lever has a longitudinal body extending between a movable end and a hinged end, the central screw turn actuator having an outer side and an inner side, the hinged end being connected via a hinge to the outer side of the central screw turn actuator, the movable end being movable between a collapsed position where the movable end is situated over the outer side of the central screw turn actuator and an un-collapsed position where the movable end is situated outwardly from the outer side of the central screw turn actuator.

9. The apparatus of claim 8, further comprising a hinge lock having a plurality of convex nubs in the first joint body (a) that are extendable into a plurality of concave recesses when the size changeable knob is rotated in the first direction in order to lock the joint bodies together and (b) that are retractable from the plurality of concave recesses when the size changeable knob is rotated in the second direction in order to unlock the joint bodies and permit relative rotation of the joint bodies.

10. The apparatus of claim 8, wherein each hinge pivots about a hinge longitudinal body, the hinge longitudinal bodies being parallel to one another and extending perpendicular to the screw, the screw axis being generally centered between the hinge longitudinal bodies.

11. The apparatus of claim 8, wherein the turn levers are collapsed in a side-by-side arrangement.

12. The apparatus of claim 11 wherein each of the longitudinal bodies of the turn levers have inner and outer edges, the inner edges being closer to the screw axis than the outer edges, the inner edges having respective contours that mate in complimentary manner when the turn levers are collapsed in the side-by-side arrangement, the longitudinal bodies having sufficient size to cover a substantial part of the outer side of the central screw turn actuator when the turn levers are collapsed.

13. The apparatus of claim 8, wherein the joint screw further comprises a screw head and a threaded nut of a shape and size to move along the threaded body, and wherein the central screw turn actuator engages the screw, and an underside of the screw head is secured to the one of first and second arms that is furthest away from the central screw turn actuator.

14. The apparatus of claim 8, further comprising a spring that imposes a separation force between first and second surfaces of the respective first and second joint bodies.

* * * * *